(12) United States Patent
Basile et al.

(10) Patent No.: US 9,950,126 B2
(45) Date of Patent: Apr. 24, 2018

(54) MEDICATION INJECTOR WITH NEAR-EMPTY ALERT

(71) Applicant: Merck Sharp & Dohme Corp., Rahway, NJ (US)

(72) Inventors: Peter A. Basile, Bloomsbury, NJ (US); Jeffrey C. Givand, North Wales, PA (US); Steven Carl Persak, Basking Ridge, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 364 days.

(21) Appl. No.: 14/650,459

(22) PCT Filed: Dec. 5, 2013

(86) PCT No.: PCT/US2013/073212
§ 371 (c)(1),
(2) Date: Jun. 8, 2015

(87) PCT Pub. No.: WO2014/093107
PCT Pub. Date: Jun. 19, 2014

(65) Prior Publication Data
US 2015/0343157 A1 Dec. 3, 2015

Related U.S. Application Data

(60) Provisional application No. 61/735,225, filed on Dec. 10, 2012.

(51) Int. Cl.
*A61M 5/50* (2006.01)
*A61M 5/32* (2006.01)
(Continued)

(52) U.S. Cl.
CPC ...... *A61M 5/5086* (2013.01); *A61M 5/31511* (2013.01); *A61M 5/31541* (2013.01);
(Continued)

(58) Field of Classification Search
CPC ........ A61M 5/3157; A61M 2005/3125; A61M 2005/3126; A61M 5/315; A61M 5/31;
(Continued)

(56) References Cited

U.S. PATENT DOCUMENTS 5,582,598 A * 12/1996 Chanoch ........... A61M 5/31551
222/309
5,899,880 A * 5/1999 Bellhouse .............. C12M 35/04
222/389

(Continued)

FOREIGN PATENT DOCUMENTS

WO WO2004078242 9/2004
WO 2006126902 A1 11/2006
(Continued)

*Primary Examiner* — Bhisma Mehta
*Assistant Examiner* — Nilay Shah
(74) *Attorney, Agent, or Firm* — John David Reilly; Gloria Fuentes (57) ABSTRACT

A medication injector that has an alert indicator that alerts the user when the medication injector is approaching near the end of its medication supply is disclosed. The alert indicator gives the user an opportunity to make preparations to obtain additional medication for the injector if there is an insufficient amount of medication in the injector to enable the user to dispense the required dosage amount with the next injection. Initially, the alert indicator is not visible to the user, but becomes visible to the user when the injector is near empty.

12 Claims, 6 Drawing Sheets (51) Int. Cl.
*A61M 5/315* (2006.01)
*A61M 5/31* (2006.01)
(52) U.S. Cl.
CPC ............ *A61M 5/32* (2013.01); *A61M 5/3155* (2013.01); *A61M 5/31535* (2013.01); *A61M 5/31578* (2013.01); *A61M 5/31583* (2013.01); *A61M 2005/3125* (2013.01); *A61M 2005/3126* (2013.01); *A61M 2205/584* (2013.01)
(58) Field of Classification Search
CPC .......... A61M 5/31525; A61M 5/31528; A61M 5/31565; A61M 5/31566
See application file for complete search history.

(56) References Cited

U.S. PATENT DOCUMENTS

| | | | | |
|---|---|---|---|---|
| 2004/0024368 A1* | 2/2004 | Broselow | .......... | A61M 5/31525 604/207 |
| 2008/0108953 A1* | 5/2008 | Moser | ............... | A61M 5/31553 604/224 |
| 2009/0264828 A1* | 10/2009 | Dette | ................ | A61M 5/31533 604/189 |
| 2009/0275915 A1 | 11/2009 | Harms et al. | | |
| 2013/0053789 A1 | 2/2013 | Harms et al. | | |

FOREIGN PATENT DOCUMENTS

| | | | | |
|---|---|---|---|---|
| WO | 2006128794 A2 | 12/2006 | | |
| WO | WO2009141004 | 11/2009 | | |
| WO | WO 2010072700 A1 * | 7/2010 | .............. | A61M 5/24 |
| WO | 2011051366 A1 | 2/2013 | | |

* cited by examiner

MEDICATION INJECTOR WITH NEAR-EMPTY ALERT

CROSS REFERENCE TO RELATED APPLICATIONS

This application claims priority to International Application No. PCT/US2013/073212, filed Dec. 5, 2013 and which claims benefit of U.S. Provisional Application No. 61/735,225 filed Dec. 10, 2012, the content of each of which is hereby incorporated by reference in its entirety.

BACKGROUND OF THE INVENTION (1) Field of the Invention

The present invention relates to injectors for administering a medication.

(2) Description of Related Art

Various types of injectors for administering a medication are known. In some cases, the injector is capable of holding medication sufficient for multiple doses. For each dose, the user selects the amount of medication to be injected, for example by dialing a dose set knob, and then injects that selected dose. This may be done for multiple doses over a period of time, until all of the medication in the injector has been dispensed.

Such injectors may be useful for various types of medication. For example, many diabetic patients self-inject insulin multiple times each day using an injector device or pen. Many such pens are operated by the patient dialing the required dose and then self-injecting the selected dosage amount. Because the patient is constantly using an injector pen on a daily basis, users will frequently require changing to a new injector when the insulin supply is exhausted. Sometimes, as the injector pen is approaching the end of its insulin supply, the injector does not contain enough insulin to provide the full dose for this last injection.

In many injectors, as the dose is being selected or dialed, the amount of the selection is indicated to the user, for example on a scale that is visible through a window of the injector housing. As the selected dose is being injected, the scale returns in accordance with the amount injected. Thus, when the full amount of the selected dose is injected, the scale returns from the selected amount back to the zero position. If less than the full amount of the selected dose is injected, the scale returns only by the amount that has been injected, such that after the partial injection the scale shows the difference between the amount selected and the amount injected.

Conventionally, there have been two ways of handling the situation when there is only a partial dose remaining in the injector pen. In the first way, the user sets the dose the same way as the prior doses, by dialing the dosage knob to the full amount of the desired dose. When only a partial dose of medication remains in the pen, this set dose exceeds the remaining amount of medication. The user may not be aware that the set dose exceeds the available medication. When the user injects the medication, the delivery mechanism will stop when the full available amount of medication has been delivered, because the piston rod inside the injector cannot advance any further. In this case, the scale of the injector pen indicates the portion of the selected dosage amount that was not dispensed, which the user must supplement with an additional injection from a new injector pen.

In the second way, an "active-stop" injector, the dosage knob prevents the user from dialing a dose that is greater than the amount of medication remaining in the pen. Thus, the injector itself will indicate to the user that only a partial dose remains, which indication will occur at the time the user attempts to set a dose higher than the amount of remaining medication.

In using both types of injector pens, the user should perceive that the old injector pen is near empty and have the new injector pen ready to inject the supplemental make-up dose. But if the user only becomes aware of the last remaining dose too late, such as only when the injector is empty or only upon attempting to dial a dose, the user may not have prepared the new injector pen for use. Because insulin pens are commonly stored in the refrigerator for preservation, an unaware user would have to retrieve a new injector from the refrigerator and administer a cold injection for the supplemental dose, which is uncomfortable. Otherwise, the user will have to wait until the new injector pen is warmed to room temperature, which can be inconvenient.

In addition, many "active-stop" injector pens have numerous parts. Certain "active-stop" injector pens can be relatively expensive to manufacture.

BRIEF SUMMARY OF THE INVENTION

The medication injector of the present invention informs the user when the medication injector is approaching near the end of its medication supply. This gives the user an opportunity to make preparations if there is an insufficient amount of medication to dispense the required dosage amount with the next injection.

With respect to terminology, the medication injector of the present invention has a proximal end and a distal end. "Distal" refers to the direction towards the patient when the injector is applied to the patient, i.e., the needle end; "proximal" refers to the opposite direction. The terms "upper" and "proximal" with respect to the medication injector are used interchangeably herein; the terms "lower," "forward," and "distal" with respect to the medication injector are used interchangeably herein.

The medication injector comprises a housing for containing a medication cartridge (e.g., ampoule or syringe) inside the housing. The housing may be a single component or multiple components that are fitted together. The injector may have other housing components such as an inner housing(s) or sleeve(s). The medication injector may be provided with or without the medication cartridge loaded inside the housing. In some embodiments, the housing houses at least the medication cartridge. For example, the housing may be a cartridge holder portion that holds the medication cartridge.

The medication injector is designed for administering multiple doses of the medication. The medication injector may be disposable, i.e., intended to be disposed when the medication cartridge is empty; or the injector pen may be reusable, i.e., it can be reloaded with another medication cartridge when empty. The medication cartridge may include a stopper and/or needle.

There is a piston rod located in the housing oriented in the longitudinal direction. The piston rod is engaged with a drive mechanism that advances the piston rod. The piston rod may be threaded. In certain embodiments, the drive mechanism rotates the piston rod such that it is driven downward in a screwing fashion. In other embodiments, the drive mechanism drives the piston rod downward without rotation of the piston rod. In either case, the piston rod pushes against a stopper inside the medication cartridge, causing medication to be dispensed out of the cartridge. The piston rod may interact with the stopper in any suitable fashion, e.g., they may together be a single unit, the piston rod may push directly against the stopper, or the piston rod may have a flange or be attached to a separate part that pushes against the stopper. The drive mechanism can be any suitable mechanism used in injection devices, and may include conventional components such as spring(s), lever(s), clutch(es), sleeve(s), latch(es), brake(s), ratchet(s), threaded insert(s), etc. The injection mechanism may be operated manually or automatically.

The piston rod has or carries an alert indicator that signals to the user that the injector is near empty. The housing has an internal viewing portion that allows the user to see inside the housing. Initially, the alert indication is not visible through the internal viewing portion. But after the piston rod is driven downward a predetermined distance, the alert indicator becomes visible through the internal viewing portion. For example, the internal viewing portion can be a window in the housing, and the alert indicator is brought into view through the window.

In another example, part of the housing can be opaque and the internal viewing portion is a part where the housing is transparent. The alert indicator may become visible as it moves down from behind the opaque part to the transparent part of the housing. Thus, the alert indicator has a hidden position in which it is generally not visible through the internal viewing portion, and the alert indicator has a visible position in which it is visible through the internal viewing portion, with the alert indicator moving from the hidden position to the visible position when the piston rod is advanced distally a predetermined distance. The injector is designed so that the alert indicator becomes visible when a certain amount of medication remains in the injector. For example, in some embodiments, this alert indicator will become visible when the medication injector has less than 60 units of medication remaining.

In one embodiment, the alert indicator is a signal nut on the piston rod that is initially located on a lower threading portion of the piston rod at a position where the signal nut is not visible to the user. On this lower threading portion, the piston rod is rotatable relative to the signal nut. The signal nut may have any suitable shape, such as square, hexagonal, or round (e.g., a disc).

As the piston rod is driven forward during actuation of the medication injector, the rod freely rotates through the signal nut, which is held stationary inside the housing. The signal nut may be held in place inside the housing by any suitable mechanism. For example, the signal nut may have spring arms that flex radially outward against a stationary component of the medication injector (e.g., inside wall of the housing).

Because the signal nut is held stationary, as the piston rod is fed through the signal nut, the signal nut travels in a relative upward direction on the piston rod as the piston rod is driven downward (although the signal nut remains stationary relative to the housing). Once the piston rod has been advanced to a position where only a certain amount of medication remains, a predetermined position on the piston rod reaches the signal nut and the signal nut becomes rotationally locked to the piston rod (such that the signal nut cannot move further toward the proximal end of the piston rod). Being rotationally locked to the piston rod, the signal nut now travels downward with the piston rod as the piston rod is driven downward. With this downward movement of the signal nut, it becomes visible to the user, indicating to the user that the medication injector is close to exhausting its supply of medication. The signal nut may have a color that makes it more conspicuous to the user. For example, the signal nut may be red or another suitable color, such as a color that is different from an external color of the housing.

The following describes an embodiment of a mechanism by which the signal nut may become rotationally locked to the piston rod. In this embodiment, the piston rod has an upper threading portion and a lower threading portion, with the thread form (cross-section shape of the threading) on the upper threading portion being narrower than the thread form on the lower threading portion. The signal nut has a hole through which the piston rod is inserted. This hole is threaded with a thread form that mates with the thread form on the lower threading portion of the piston rod, but interferes (does not mate) with the thread form on the upper threading portion of the piston rod. In some cases, the length of the piston rod having the wider thread form (on the lower threading portion) is greater than the length of the piston rod having the narrower thread form (on the upper threading portion). For example, a majority of the length of the piston rod may have the wider thread form (on the lower threading portion).

In this embodiment, the signal nut is initially located on the lower threading portion of the piston rod with the wider thread form. However, as the piston rod is fed downward through the signal nut, which remains stationary at this stage, the upper threading portion of the piston rod having the narrower thread form approaches the signal nut. But because the internal threading on the signal nut interferes with the thread form on the upper threading portion of the rod, the upper threading portion of the rod cannot rotate through the signal nut (i.e., an interfering interaction). As a result, the signal nut becomes rotationally locked to the piston rod and travels axially downward with the piston rod. This downward travel of the signal nut brings it into a position where it is visible to the user, indicating to the user that the medication injector is near-empty.

Various components involved in this mechanism can be configured to give the near-empty signal at the appropriate time, including the location of transition to the narrower thread form on the upper threading portion of the piston rod, the length of the piston rod, the width of the signal nut, the location and size of the view window, etc. The injector may be designed so that the alert indicator becomes visible when less than a single dose of medication remains in the injector. In some embodiments, this signal nut will become visible when the medication injector has less than 60 units of medication remaining.

In an alternate embodiment of the medication injector, the alert indicator is on the piston rod or is a part of the piston rod itself. For example, the piston rod may have a different color on an upper portion than a lower portion. Appearance of the upper portion in a different color signals that the injector is near empty. As the piston rod advances downward, the alert indicator on the piston rod is brought into a position where it is visible to the user, alerting the user that the medication injector is near-empty. The indicator may be made visible through an internal viewing portion, as described above.

Because the medication injector of the invention is designed to alert the user when it is near-empty, it may have a finer resolution dosage scale than conventional medication injectors. Typical insulin injectors deliver a maximum single dose of 60 units, and, as such, may have dosage scale markings in coarse increments, such as 60 units.

In contrast, in some embodiments, the medication injector of the invention may have a dosage scale with finer increments to inform the user more precisely about the dosage amount remaining when the medication injector is near-empty. For example, the dosage scale may include markings with increments of 20 units or finer, or in some cases, in increments of 10 units or finer. With this finer resolution dosage scale, the user can be better informed about the amount of medication remaining.

In another embodiment, the present invention provides a method of administering a dosage amount of medication using a medication injector. The method comprises visualizing an alert indicator in the medication injector. After visualizing the alert signal, the user retrieves another (second) medication cartridge for loading in the medication injector or another (second) medication injector. The user performs an injection with the (first) medication injector to administer part of the dosage amount of the medication. To complete the dosage amount, the user then performs another injection with the medication injector loaded with the second medication cartridge or with the second medication injector.

DETAILED DESCRIPTION OF THE INVENTION

Figure 1:
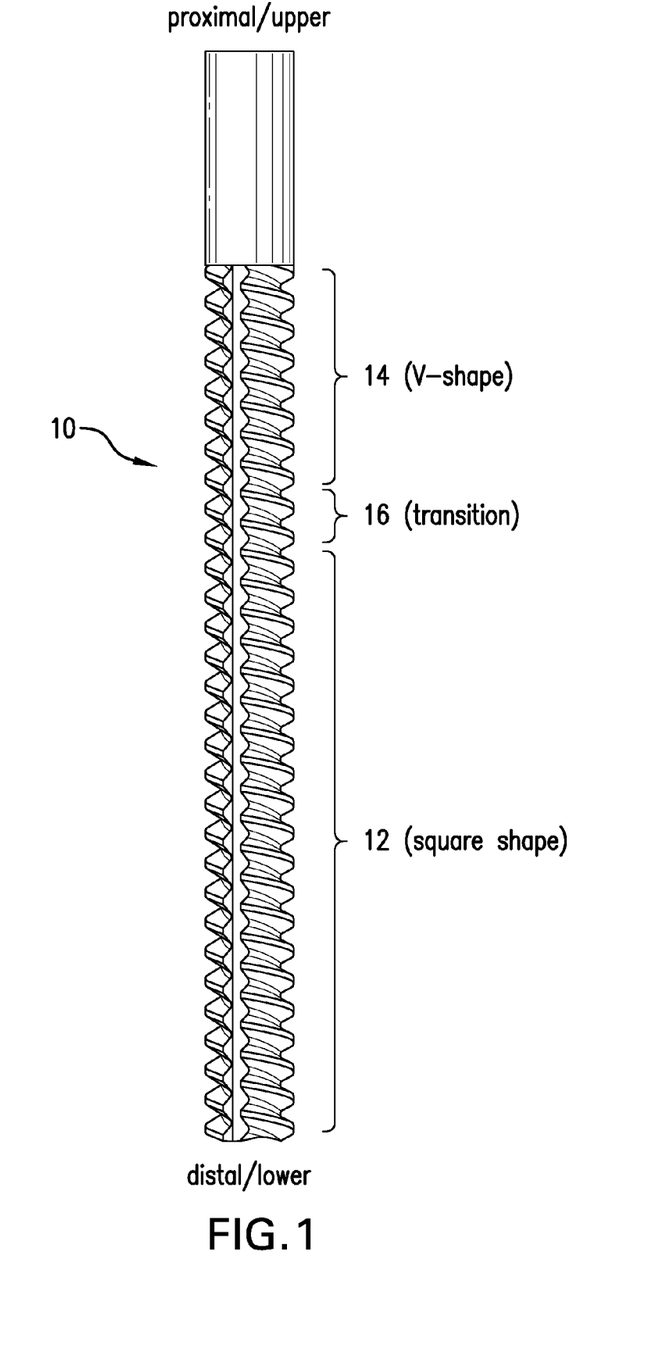
FIG. 1 shows a piston rod according to an embodiment.

An example embodiment of the invention will now be described. FIG. 1 shows an example of a piston rod 10. Piston rod 10 is threaded and has two different thread forms. On the lower threading portion 12 of rod 10, the thread form is a square shape. On the upper threading portion 14 of rod 10, the thread form is a narrower width, V-shape. The threading on lower portion 12 is continuous with the threading on upper portion 14. The transition 16 between the two thread forms may be gradual or abrupt.

Figure 2:
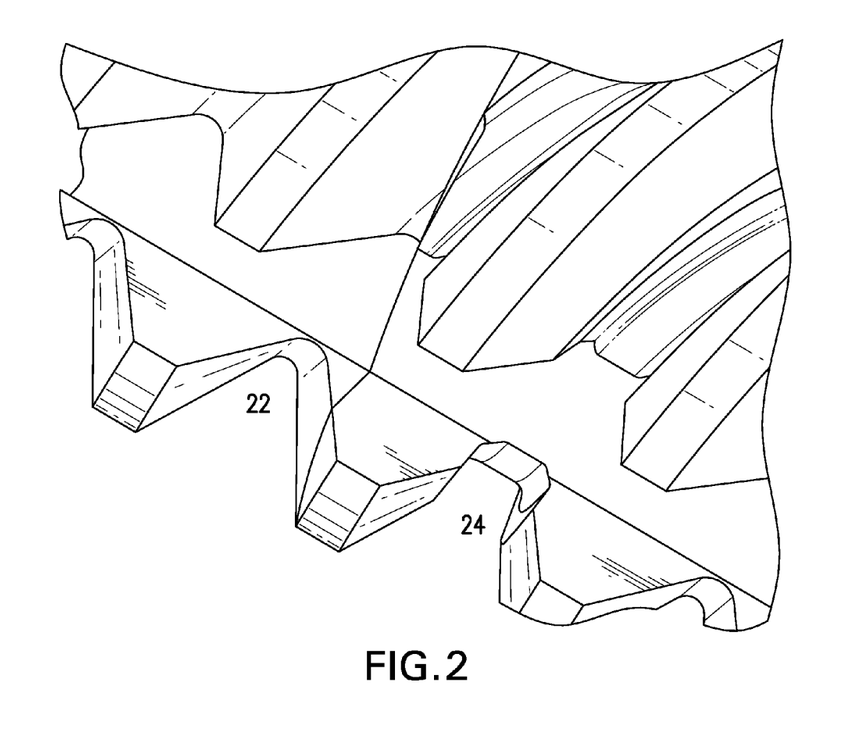
FIG. 2 shows a close-up view of the two different thread forms on the piston rod of FIG. 1.
Figure 3:
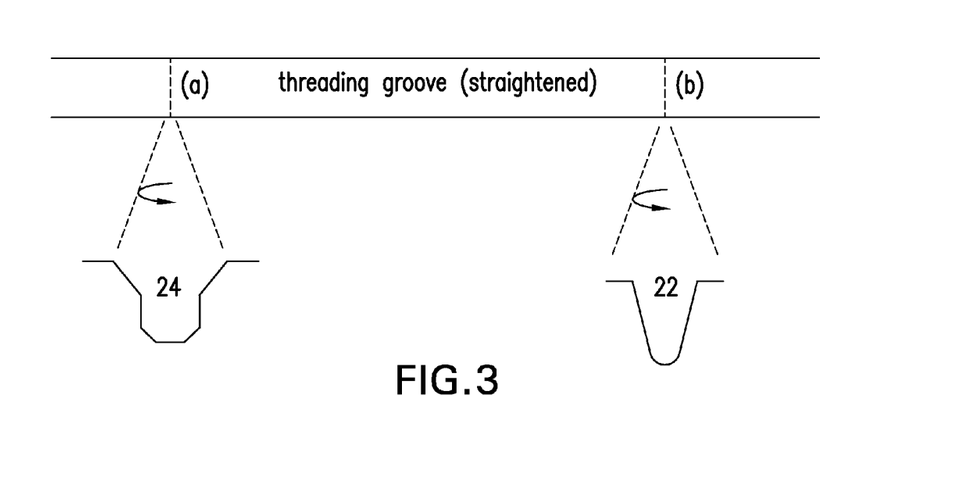
FIG. 3 shows the threading groove on the piston rod of FIG. 1 if it were to be unwound into a straight path.

FIG. 2 shows a close-up view of the two different thread forms at the transition point 16. As seen here, the thread form 22 on the upper threading portion 14 of piston rod 10 is V-shaped, and the thread form 24 on the lower threading portion 12 is square-shaped. FIG. 3 shows the threading groove on rod 10 if it were to be unwound into a straight path. At points (a) and (b), transverse cross-section views of the groove (turned 90°) are shown. At point (a) on the lower threading portion 12 of rod 10, the cross-section view shows the square-shaped thread form; at point (b) on the upper threading portion 14 of rod 10, the cross-section view shows the narrower V-shaped thread form.

Figure 4:
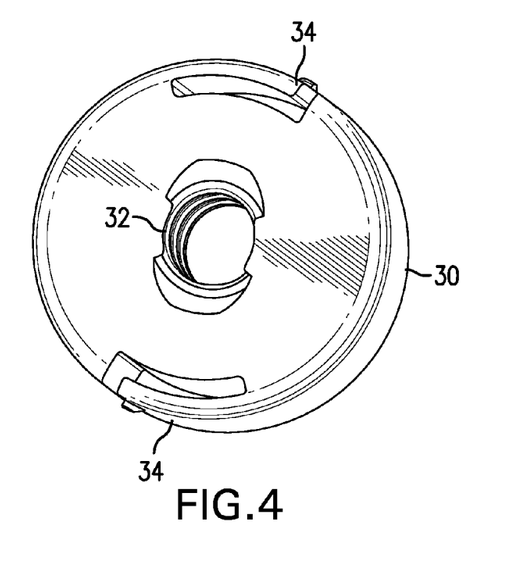
FIG. 4 shows a signal disc according to an embodiment.
Figure 5:
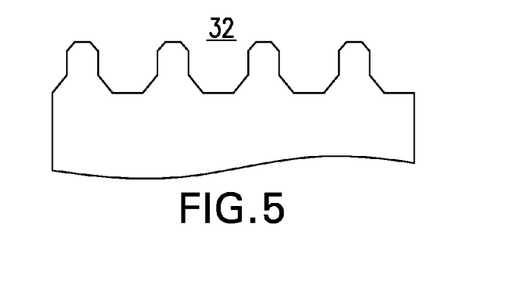
FIG. 5 shows a cross-section view of the internal threading of the signal disc in FIG. 4.

FIG. 4 shows an example of a signal nut of the present invention, in the form of a red-colored or another suitable colored disc 30 which has a threaded hole 32 through which the rod 10 is inserted. The disc 30 has two spring arms 34 that flex radially outward against a fixed object inside the housing to keep the disc 30 stationary in the housing until the signal nut becomes rotationally locked to the piston rod 10 and the torque applied to the piston rod, and thereby to the signal nut, overcomes the holding force provided by the spring arms 34. The spring arms 34 may have detent projections that mate with corresponding depressions on the inside surface of the housing or another stationary component, to keep the disc 30 stationary until it becomes rotationally locked to the piston rod 10 and sufficient force is applied. FIG. 5 shows a cross-section view of the internal threading of hole 32. Viewed together with FIG. 3, this demonstrates that the thread form of the internal threading in hole 32 has a square-shape that mates with the square-shaped thread form 24 of lower threading portion 12 of rod 10, but interferes with the narrower V-shaped thread form 22 on the upper threading portion 14.

Figure 6:
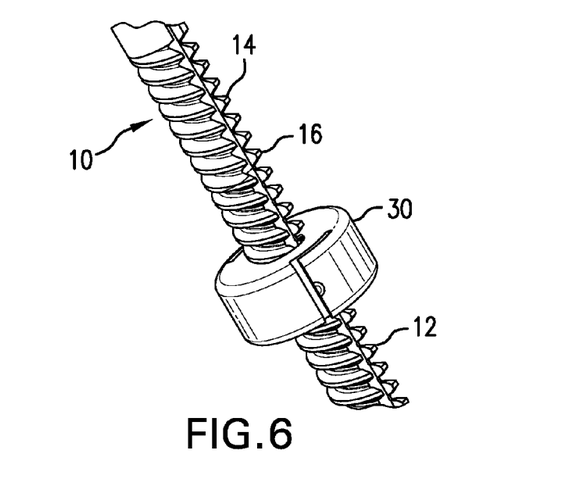
FIG. 6 shows the piston rod of FIG. 1 inserted through the signal disc of FIG. 4.

FIG. 6 shows the piston rod 10 inserted through threaded hole 32 of disc 30. Disc 30 is initially located on a lower threading portion 12 of rod 10 (below transition point 16). At this position, because the internal threading on disc 30 mates with the lower threading portion 12 on rod 10, piston rod 10 is freely rotatable through disc 30. As the piston rod 10 screws down through disc 30, the position of the threads of the piston rod 10 relative to the disc 30 changes, such that the upper threading portion 14 of rod 10 moves toward the disc 30. When the upper threading portion 14 of rod 10 reaches the disc 30, the V-shaped threading on this portion of rod 10 interferes with the internal threading on disc 30. This blocks the rod 10 from further rotating through the disc 30, such that further rotation of the rod 10 will carry the disc 30 with it.

Figure 7A:
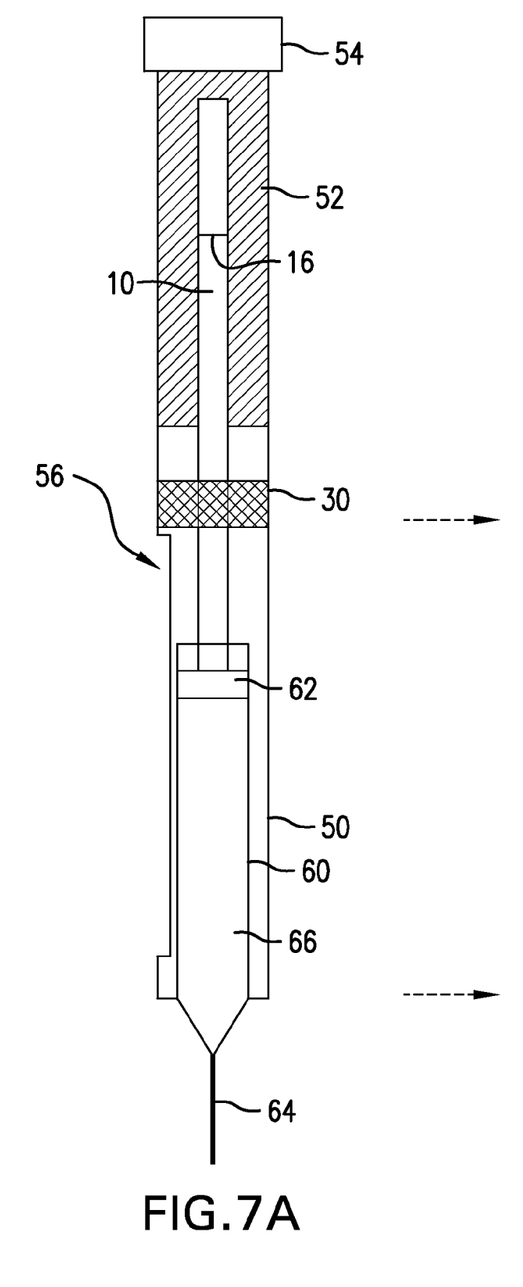
FIG. 7A shows a cross-section view of a medication injector according to an embodiment.
Figure 7B:
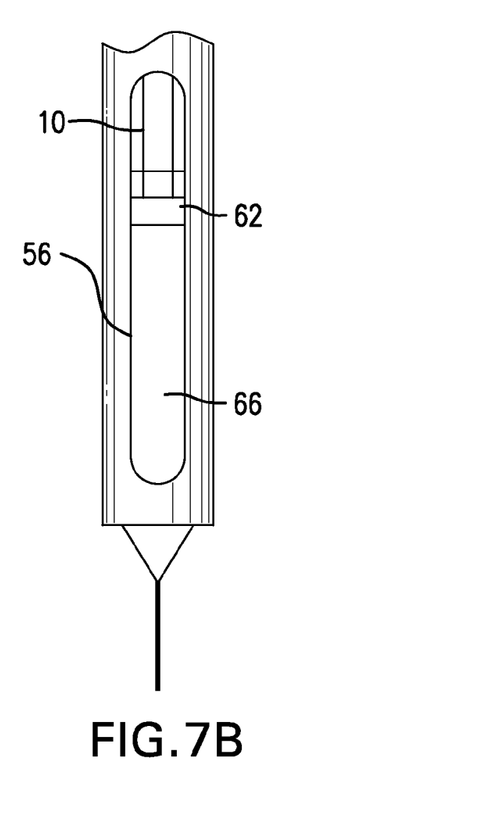
FIG. 7B shows a side view of the lower portion of the medication injector.
Figure 8:
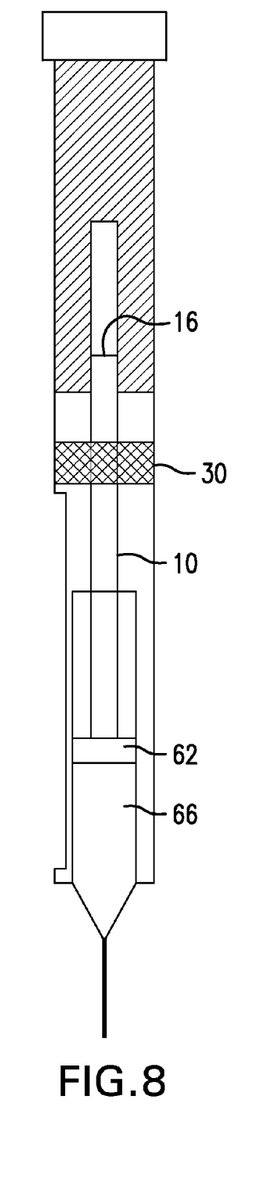
FIG. 8 shows the injector of FIG. 7 after several injections.
Figure 9A:
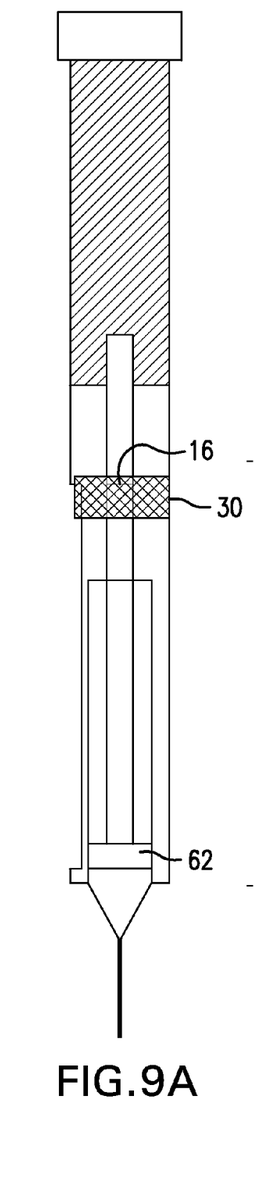
FIG. 9A (cross-section) and FIG. 9B (side view) show the injector of FIG. 7 when it is near empty.
Figure 9B:
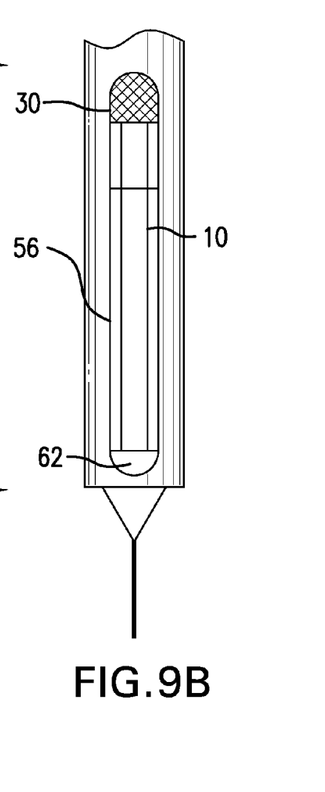

FIGS. 7-9 show an example of the functioning of one embodiment of a medication injector of the invention. As shown in FIG. 7A, the medication injector comprises a housing 50 (shown in cross-section). At the top of the medication injector, there is a dosage selection knob 54 that the user turns to dial the desired dosage amount. The housing 50 contains the piston rod 10 with disc 30 threaded thereon.

A drive mechanism 52 drives the piston rod 10 down during the dispensing of each dose. In one embodiment, the drive mechanism 52 includes a piston rod drive which rotates the piston rod 10 and a stationary threaded bushing (not shown) through which the piston rod 10 rotates. As the piston rod drive rotates, the piston rod 10 is caused to rotate, which, by virtue of the threaded engagement with the threaded bushing, feeds the piston rod 10 forward to dispense the medication. This threaded bushing allows free rotation of the piston rod 10 on both of its thread forms. The drive mechanism 52 may include other components, as explained above. Examples of drive mechanisms that can be used with the invention include those used in the SoloSTAR®-type medication injectors and those described in U.S. Pat. No. 7,918,833, U.S. Pat. No. 7,291,132, and WIPO Publication WO 99/38554, which are incorporated by reference herein.

Loaded into the distal portion of housing 50 is an ampoule or syringe 60 that contains a liquid medication 66 for dispensing through needle 64. The liquid medication 66 is pushed forward by a stopper 62, which is driven by the distal end of piston rod 10. There is a cut-out window 56 on a lower portion of the housing 50. As seen in the side view of FIG. 7B, the ampoule or syringe 60, stopper 62, and piston rod 10 are visible through cut-out window 56. At this point, the alert indicator, which is disc 30, is in a hidden position in which it is generally not visible through the window 56, and thus the disc 30 cannot be seen in FIG. 7B.

FIG. 8 shows the medication injector after several injections. With each successive injection, more of piston rod 10 is advanced forward. Therefore, the length of the piston rod 10 that has been fed forward represents the total amount of medication 66 that has been dispensed thus far. As seen here, the piston rod 10 has been advanced forward and pushed down stopper 62. However, the position of disc 30 has not changed, which is at this point is still held in place by spring arms 34 that flex outward against the inside wall of housing 50. The transition point 16 on rod 10 has not yet reached the disc 30, and the disc 30 remains in the hidden position.

FIGS. 9A and 9B show the medication injector after several more injections and in a near-empty state. The piston rod 10 has advanced further, and the transition point 16 on rod 10 has reached the disc 30. Accordingly, in the manner already explained above, the internal threading on disc 30 now has an interfering interaction with the V-shaped thread form on the upper threading portion 14 of rod 10. This causes the disc 30 to become rotationally locked to the piston rod 10. Under the driving force of the piston rod 10, the engagement of spring arms 34 on disc 30 against the inside wall of housing 50 holding disc 30 in place is overcome. Thus, disc 30 travels downward with rod 10 such that disc 30 becomes visible through the cut-out window 56 in housing 50. As can be seen in FIG. 9B, the alert indicator, which is disc 30, has been moved from the hidden position to the visible position in which it is visible through the window 56. This alerts the user that the medication injector is in near-empty condition. Once alerted by the alert indicator, the user can then read the dosage scale and check the amount of medication remaining in the pen. If the remaining amount is insufficient to deliver the full dosage requirement, the user can retrieve a new medication injector (or new medication cartridge for reloading the medication injector) from the refrigerator and warm it room temperature so that it can be used to supplement the final dose from the nearly-depleted medication injector (or medication cartridge).

In the above-described embodiment, the spring arms 34 on disc 30 drag against the inner wall of housing 50 to prevent the disc 30 from rotating down on piston rod 10, which might give the appearance of a broken or disconnected part. But in an alternate embodiment, the spring arms 34 on disc 30 may be designed to avoid dragging against the inner wall of housing 50 (or other component) as the disc 30 is released from its stationary restraint and advanced downward. In this case, when disc 30 is released from its stationary hold, it may spin freely downward on rod 10 under the force of gravity to bring the disc 30 into a position where it is visible to the user. This may give a more dramatic visual signal to the user that the medication injector is near-empty. Moreover, the disc 30 may be sized to be smaller than the diameter of syringe 60. With this design, when disc 30 spins down on rod 10, the disc 30 would come to rest on top of stopper 62.

Figure 10:
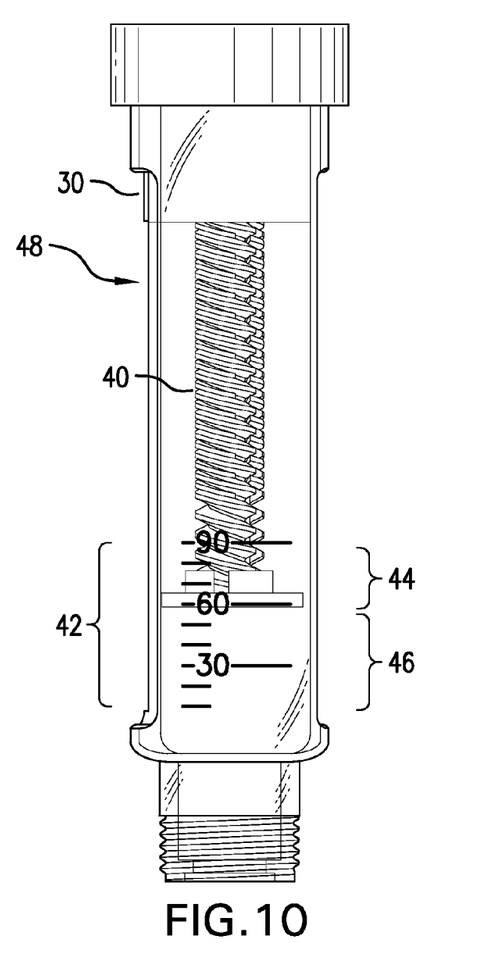
FIG. 10 shows a cartridge holder portion of a medication injector according to another embodiment.

In another embodiment of the invention, FIG. 10 shows a cartridge holder portion for a medication injector. Inside the cartridge holder, there is a medication cartridge made of transparent glass and a piston rod 40 that is visible through the glass. The cartridge holder portion is made of transparent plastic and has a window 48. When the red (or another suitable color) disc 30 comes into view, it is visible through the window 48 as well as through the transparent cartridge holder. The dosage scale 42 on the medication cartridge is also visible through the transparent cartridge holder. The level at the bottom of the flange of rod 40 is the dosage amount remaining in the medication cartridge.

The medication cartridge has a narrower dosage scale than conventional cartridges. As shown in FIG. 10, the dosage scale measures only the final 90 units of medication in the cartridge. Having a narrower dosage scale can be advantageous because it helps to draw attention to the dosage scale when the injector is approaching empty. Moreover, to highlight the final (or near-final) dosage amount, the last 60 units may be marked in red color (or another suitable color) (bracket 46) compared to the black color markings for the dosage amount above 60 units (bracket 44).

As such, in some embodiments of the medication injector, the injector has a dosage scale that measures the amount of medication contained in the medication cartridge, and the maximum amount measured by the dosage scale is 120 units or less. For example, the dosage scale may be limited to a range of 0 to 90 units or limited to a range of 0 to 60 units. In some embodiments, a lower range of the dosage scale is shown in a different color than an upper range of the dosage scale. For example, in the dosage scale, the dosage range of 60 units and less can be marked in a different color (e.g., red color) than the markings for the dosage amounts greater than 60 units (e.g., black color).

In some embodiments, a lower range of the dosage scale has markings in finer resolution increments than an upper range of the dosage scale. For example, in the dosage scale, the dosage markings in the range of 0 to 60 units can be in finer resolution (e.g., increments of 10 units) than the dosage markings above 60 units (e.g., increments of 30 units). This can allow the user to more precisely measure the final (or near-final) dosage amount to be injected.

Figure 11:
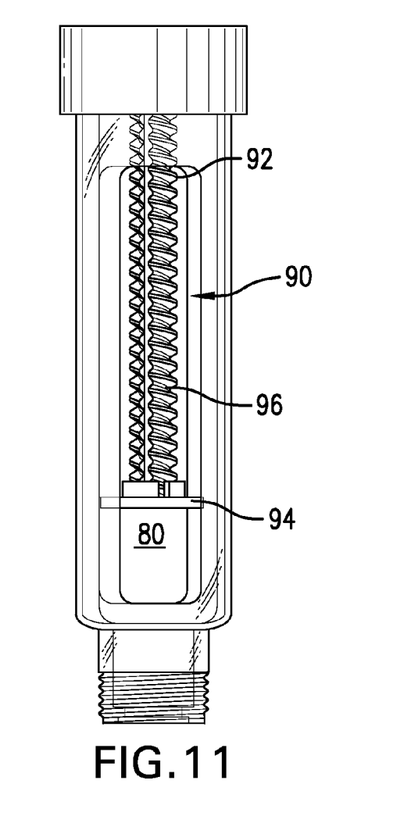
FIG. 11 shows a cartridge holder portion of a medication injector according to yet another embodiment.

FIG. 11 shows a partial view of an alternate embodiment of a medication injector in which the piston rod 90 has a different color on an upper portion 92 than on a lower portion 96 of the rod 90. As the piston rod 90 advances downward, appearance of the differently-colored upper portion 92 through window 80 and the transparent cartridge holder signals to the user that the injector is near empty.

While certain embodiment illustrated herein have been described with respect to a piston rod that rotates during dose delivery, it will be understood that an alert indicator according to the invention can be utilized with a piston rod that advances axially without rotation during dose delivery. The piston rod may have an alternative catch mechanism to the interfering threads as previously described. For example, the piston rod may have a lug, abutment, tab or other catch mechanism near its proximal end. The alert indicator or signal nut may have a mechanism for temporarily holding the alert indicator or signal nut in place until the catch mechanism of the piston rod advances far enough to engage and dislodge the alert indicator or signal nut. Alternatively, a piston rod that advances axially without rotation during dose delivery may have an upper portion with a different color, similar to the embodiment of FIG. 11, wherein the differently-colored portion serves as the alert indicator.

In some embodiments, the medication injector of the present invention includes instructions for use that instruct the user to read the remaining dosage amount in the medication cartridge (at the distal edge of the stopper) when the alert indicator appears and confirm whether this amount is sufficient for the full dose that the user requires. The medication injector of the present invention can be used to inject insulin or any other medication that is administered by injection.

The foregoing description and examples have been set forth merely to illustrate the invention and are not intended to be limiting. Each of the disclosed aspects and embodiments of the present invention may be considered individually or in combination with other aspects, embodiments, and variations of the invention. In addition, unless otherwise specified, the steps of the methods of the present invention are not confined to any particular order of performance. Modifications of the disclosed embodiments incorporating the spirit and substance of the invention may occur to persons skilled in the art, and such modifications are within the scope of the present invention.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

We claim:

1. A medication injector for injecting a medication comprising:
    a housing having a longitudinal axis and an internal viewing portion for viewing inside the housing;
    a piston rod in the housing and oriented in a direction of the longitudinal axis wherein the piston rod has an upper threading portion and a lower threading portion that is located distal to the upper threading portion, the upper threading portion having a thread form that is different than a thread form on the lower threading portion; and
    an alert indicator on or carried by the piston rod for signaling that the injector is approaching an end of a medication supply, the alert indicator having a hidden position in which it is generally not visible through the internal viewing portion and a visible position in which it is visible through the internal viewing portion, the alert indicator moving from the hidden position to the visible position when the piston rod is advanced distally a predetermined distance; wherein the alert indicator is a signal nut having a threaded hole through which the piston rod is inserted, the signal nut mating with and being rotatable on the lower threading portion of the piston rod, but interfering with and not rotatable on the upper threading portion of the piston rod.

2. The injector of claim 1, wherein the signal nut is initially located on the lower threading portion of the piston rod at a position where the signal nut is in the hidden position and is not visible through the internal viewing portion, and wherein the signal nut moves relatively proximally on the piston rod as the piston rod is driven distally.

3. The injector of claim 2, wherein the signal nut is held stationary in the housing while on the lower threading portion, and wherein the signal nut travels distally with the piston rod once the upper threading portion reaches the signal nut.

4. The injector of claim 1, wherein the signal nut has a different color than an external color of the housing around the internal viewing portion.

5. The injector of claim 1, wherein a length of the piston rod encompassed by the lower threading portion is greater than a length of the piston rod encompassed by the upper threading portion.

6. The injector of claim 5, wherein the lower threading portion encompasses a majority of an entire length of the piston rod.

7. The injector of claim 1, wherein the signal nut has flexible arms that flex outward.

8. The injector of claim 1, wherein the medication is insulin.

9. The injector of claim 1, wherein the injector has a dosage scale for indicating an amount of the medication in the injector, wherein the dosage scale is marked in increments of 30 units or less.

10. The injector of claim 9, wherein a maximum amount measured by the dosage scale is the last 120 units or less of the medication amount.

11. The injector of claim 9, wherein a lower range of the dosage scale is shown in a different color than an upper range of the dosage scale.

12. The injector of claim 9, wherein a lower range of the dosage scale has markings in finer resolution increments than an upper range of the dosage scale.

* * * * *